United States Patent

Malamud et al.

[11] Patent Number: 4,460,833
[45] Date of Patent: Jul. 17, 1984

[54] RADIATION SHIELDED WHEEL PATIENT TRANSPORT

[75] Inventors: Herbert Malamud, Westbury; Herman Glasser, Manhasset Hills, both of N.Y.

[73] Assignee: Victoreen, Inc., Cleveland, Ohio

[21] Appl. No.: 341,611

[22] Filed: Jan. 22, 1982

[51] Int. Cl.³ .............................................. G21F 3/00
[52] U.S. Cl. .............................. 250/519.1; 250/515.1
[58] Field of Search ........................... 250/519.1, 515.1

[56] References Cited

U.S. PATENT DOCUMENTS 3,622,432  11/1971  McCluer et al. ............ 250/519.1 X
3,984,695  10/1976  Collica et al. ............... 250/519.1 X Primary Examiner—Alfred E. Smith
Assistant Examiner—Jack I. Berman
Attorney, Agent, or Firm—Fraser, Barker, Purdue & Clemens

[57] ABSTRACT

A shield device attached to wheel patient support apparatus between a patient and an attendant, the shield device including radiation shielding material extending across wheel patient support in such a manner that attendants are shielded from the patient.

1 Claim, 5 Drawing Figures

RADIATION SHIELDED WHEEL PATIENT TRANSPORT

BACKGROUND OF THE INVENTION

1. Field of the Invention

This invention generally relates to wheel patient supports such as wheel chairs, and wheel stretchers and the like and, more particularly, to wheel patient supports including attendant radiation shield devices.

2. Description of the Prior Art

In nuclear medicine departments it is common practice to transfer patients in wheel chairs and/or stretchers from their room in a hospital to the nuclear medicine department for a "scan" or other examination. Prior to sending patients to this department the procedure may be to inject them with radioisotopes. Depending on the type of "scan" or other examination to be performed, the radioisotopes will be directed to a specific portion of the patient's body.

For example, if it is a "brain scan" then most of the injected radioisotope will travel towards the patient's head. Thus, when the patient is placed in the wheel chair or on a stretcher, there will be a fair amount of radiation emanating from the head of the patient which will "strike" the hospital attendant who is pushing the wheel chair or stretcher. Although the amount of radiation received by the attendant is normally considered of a low level and not dangerous, it is common practice in the nuclear medicine field to minimize radiation exposure and to observe a concept commonly called "ALARA", that is, maintaining such radiation "as low as reasonably achievable".

Accordingly, it is desirable to produce radiation shield devices for use with wheel chairs, wheel stretchers and the like wherein radiation emanating from radioisotope injected patients will not impinge upon the attendant wheeling the patient.

SUMMARY OF THE INVENTION

As contemplated by the invention, a radiation shield is mounted on a wheel patient support apparatus in a position to shield an attendant from a radioistope injected patient. The radiation shield may typically include a sheet of vinyl or other material having attached thereto, such as by sewing, a sheet of lead containing vinyl material such as is used for protective aprons used by radiologic physicians. In other forms, the radiation shield may typically include a thin sheet of lead, tungsten foil or like material which may be cemented or otherwise attached to a rigid member supported from the wheel support apparatus. When vinyl sheet material is employed, opposite marginal edges of the protective sheet may be suitably attached directly to elements of the wheel support apparatus or frame means may be provided which can be detachably secured to the wheel patient supports.

In one illustrated embodiment of the invention, the back of a conventional collapsable wheel chair used in nuclear medicine examinations which is composed of vinyl or other material, may typically include a sheet of radiation shielding material containing a base having a lead equivalence of one (1) millimeter. In this instance, the wheel chair is provided with means for supporting the radiation shield so as to form an extension head rest which extends from a point below the protective wheel chair back, to a position approximately five inches (125 millimeters) above the patient's head. Preferably, the shielding material of the backrest and extension should be formed as one piece.

In another illustrated embodiment of the invention each end of a wheel stretcher may be provided with a radiation shield which extends from a point below the horizontal patient support surface to a height wherein the attendant is shielded from radiation emanating from a supine patient.

An object of the invention is to produce a radiation shield for wheel patient supports which is simple in construction, inexpensive to manufacture, and efficient in operation.

BRIEF DESCRIPTION OF THE DRAWINGS

The above as well as other objects of the invention will become readily apparent to one skilled in the art from reading the following detailed description of the preferred embodiments of the invention when considered in the light of the accompanying drawings in which.

DETAILED DESCRIPTION OF THE PREFERRED EMBODIMENTS

Figure 1:
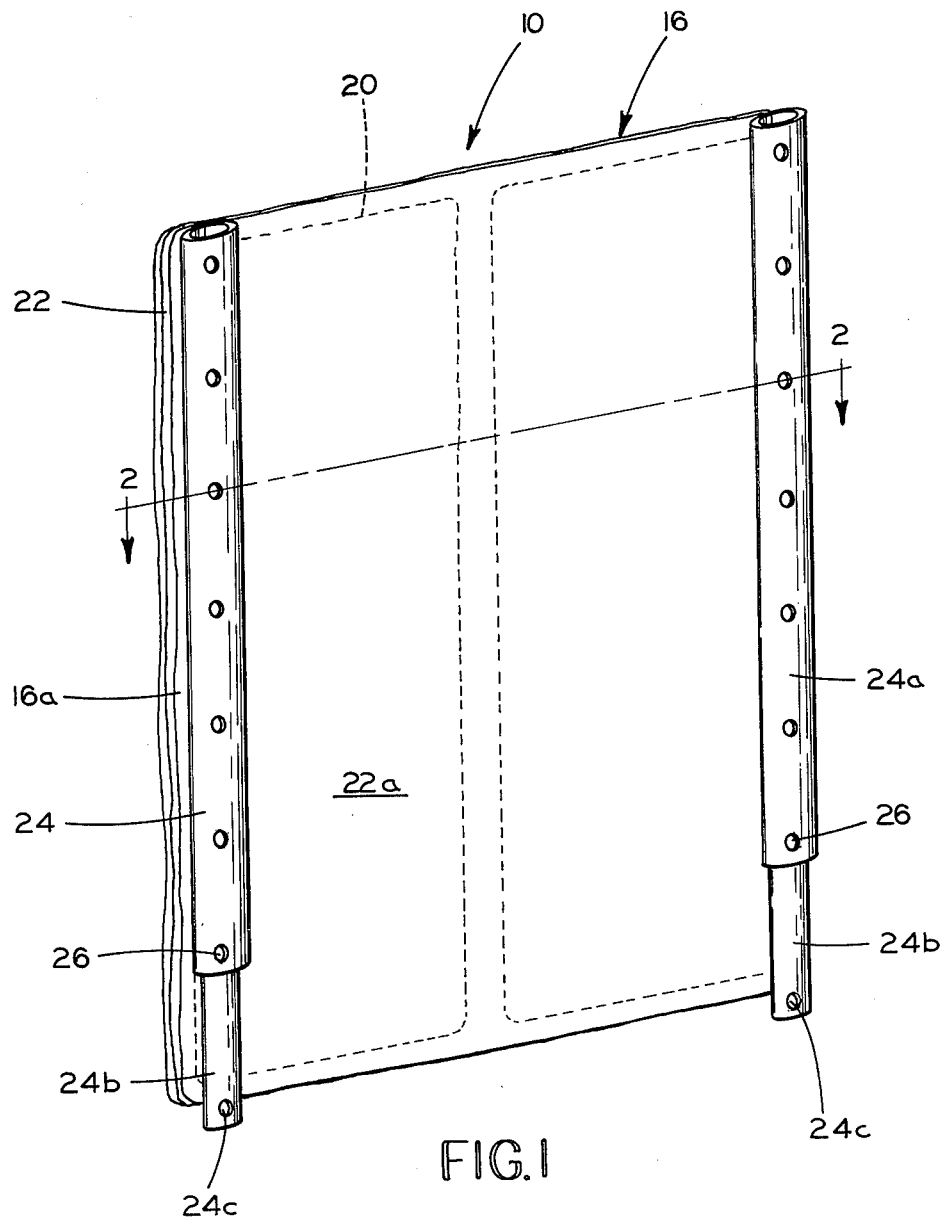
FIG. 1 is an enlarged perspective view of a radiation shield attachment constructed in accordance with the invention.
Figure 2:
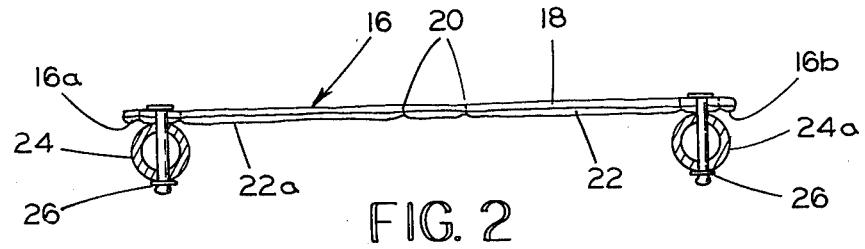
FIG. 2 is a cross-sectional view taken substantially along line 2—2 in FIG. 1.

Referring to the drawings, particularly FIGS. 1 and 2, wherein like reference numerals designate similar parts throughout, there is illustrated a radiation shield 10 adapted to be utilized with wheel patient supports such as a wheel chair 12 (see FIG. 3) and a stretcher 14 (see FIG. 5) to transport patients from their rooms to the nuclear medicine departments in hospitals.

As illustrated in FIGS. 1 and 2, the radiation shield attachment 10 generally includes a laminated sheet structure 16 comprising a sheet of vinyl or like material 18 having attached thereto, as by stitches 20, a sheet of lead containing vinyl material 22 having a lead equivalence appropriate to its intended use and two like support legs 24 and 24a disposed along opposite marginal edges 16a and 16b of the laminate structure 16. Preferably, the legs 24 and 24a are tubular members, cylindrical in shape, which are secured to the opposite marginal edges 16 and 16a respectively, on the back face 22a of the lead containing vinyl sheet 22 by a row of conventional fasteners such as snap fasteners 26. The lower ends of legs 24a may be reduced in diameter as at 24b to cooperate with sockets to be described hereinafter, and which are affixed to the wheel patient supports. The reduced leg portions 24b may be provided with apertures 24c, the purpose of which will be described hereinafter.

Figure 3:
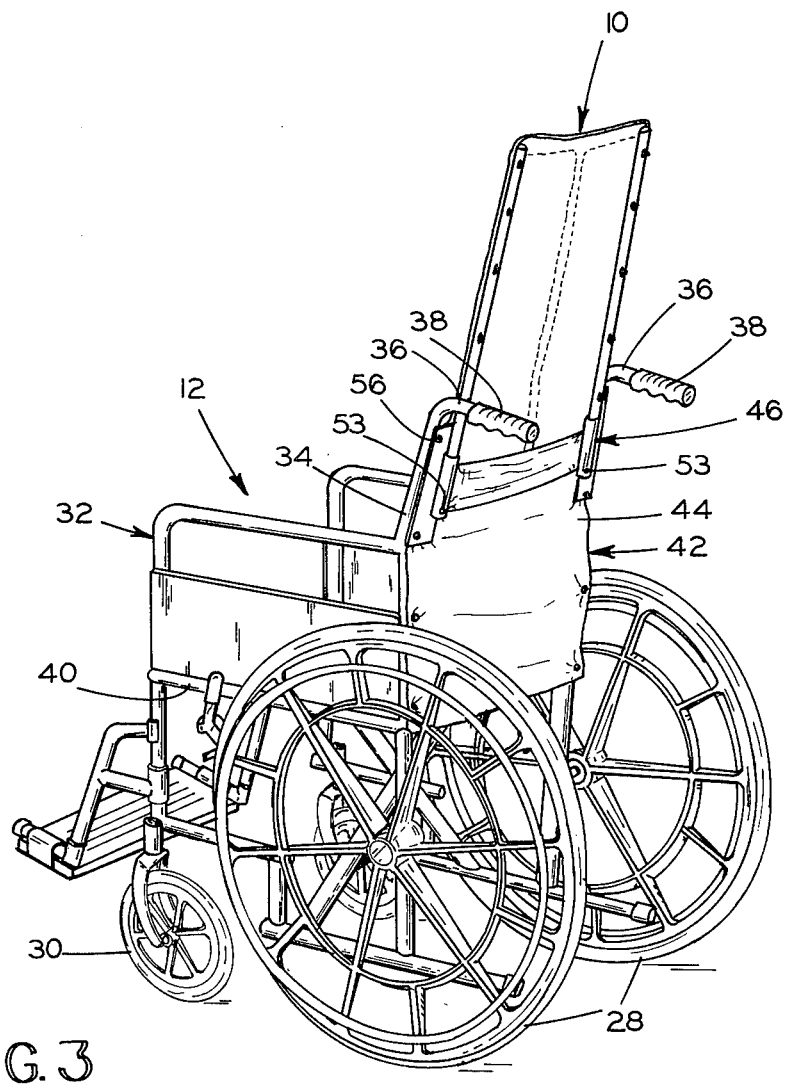
FIG. 3 is a perspective view of a wheel chair incorporating the radiation shield attachment illustrated in FIG. 1.
Figure 4:
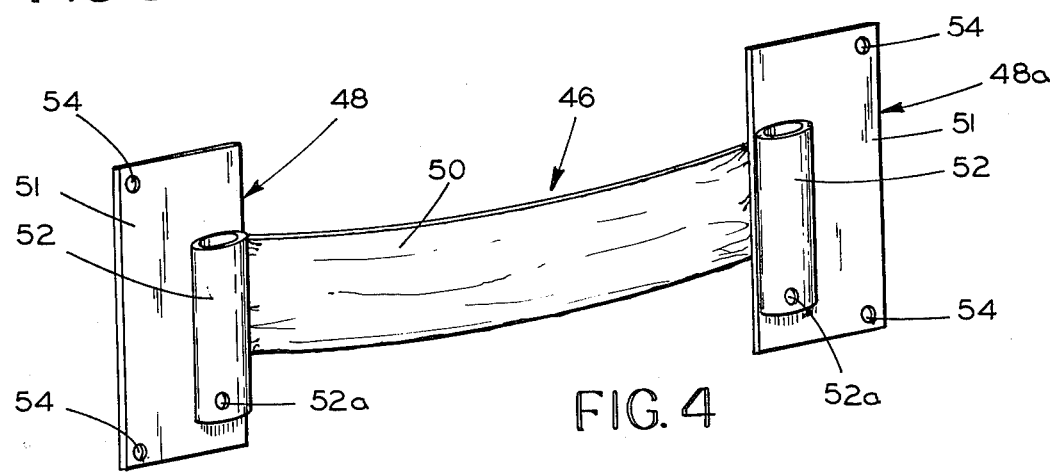
FIG. 4 is an enlarged perspective view of the support device adapted to be affixed to the back of the wheel chair illustrated in FIG. 3 for receiving the radiation shield attachment illustrated in FIG. 1.

Referring now to FIG. 3, the wheel chair 12 is commonly formed of hollow tubing and includes a pair of large rear support wheels 28, a pair of smaller front caster wheels 30 for supporting the overall wheel chair frame 32. Included within the frame 32 are upright backrests support members 34 terminating in rearwardly extending handles 36 having grips 38. Another portion of the frame 32 is composed of seat support members 40 which are utilized to mount a seat (not shown).

In this embodiment of the invention, the backrest portion 42 of the wheel chair 12 is preferably an extension of the sheet structure 16. However, the portion 42 may be formed of a laminated sheet structure 44 also including a sheet of lead based vinyl material as described above. The laminated structure 16 or 44 is configured to extend between and is suitably attached as by the snap fasteners 26, to the upright legs 24 and 24a and backrest members 34 of the wheel chair frame 32. As illustrated in FIG. 3, the radiation shield 10 may be detachably mounted or permanently attached on the wheel chair 12 by a socket support member 46 which is affixed to the upright backrest support members 34. More specifically, the socket support member 46 includes a pair of spaced, flange socket members 48 and 48a and may also include a flexible fabric support strip 50 or the like disposed over the overlapping portions of members 16 and 44 when the shielding material is formed of two pieces. Each flange socket member 48 and 48a includes a flat rigid rectangularly shaped plate member 51 and a cylindrical tubular socket member 52 affixed along one marginal edge of the plate 51 as by welding. The socket member 52 may be provided with an aperture 52a alignable with the apertures 24c for receiving a self-tapping metal screw 53 (see FIG. 3) which attaches the members together. The opposite marginal edge of plate 51 is provided with a pair vertically aligned spaced apertures 54 for receiving machine screws 56 or the like for attaching the flange socket members 48 and 48a to the wheel chair backrest support members 34. It will be noted that the inside diameter of the socket members 52 is selected to correspond to the outside diameter of the reduced portion of the legs 24 and 24a of shield attachment 10 for snugly receiving them.

Figure 5:
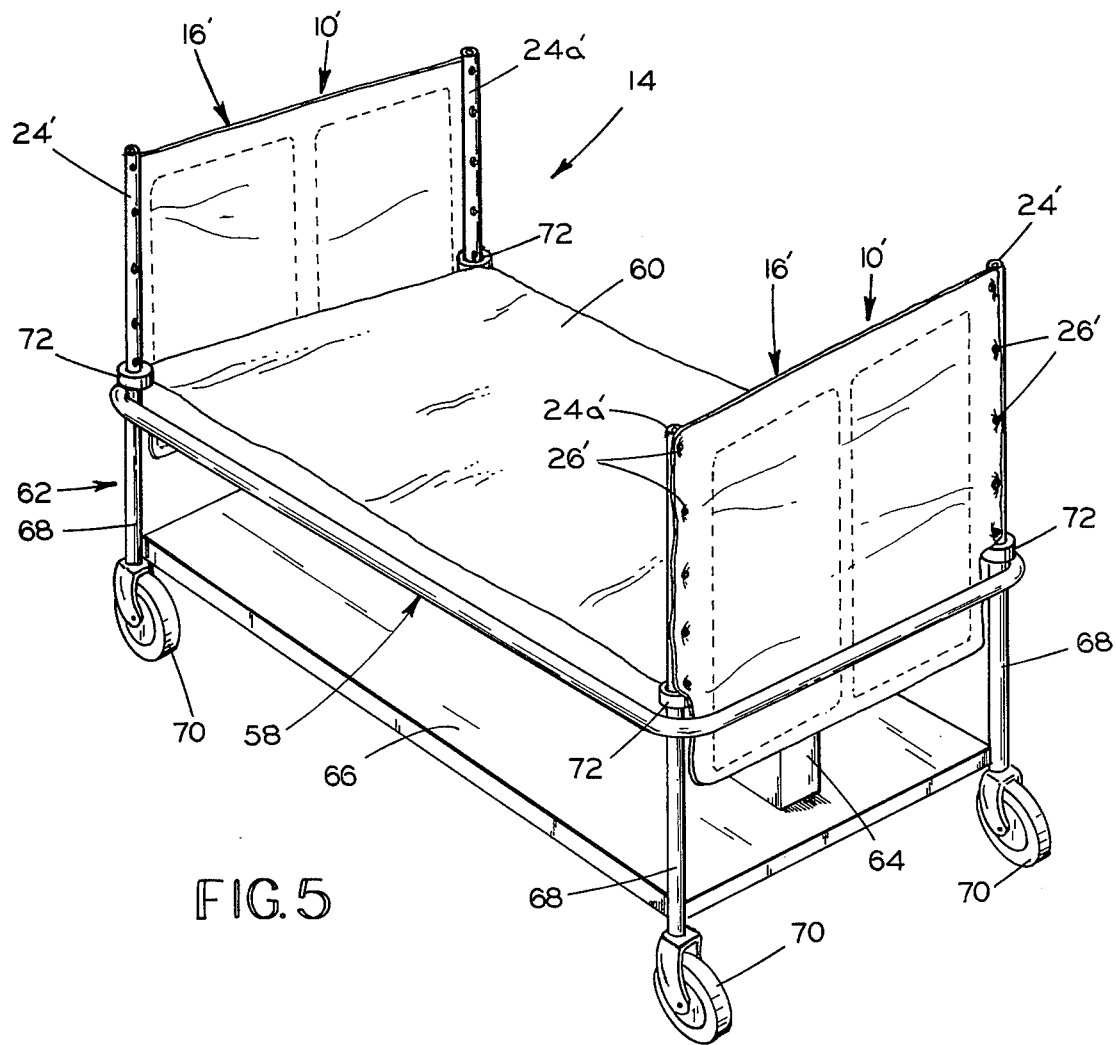
FIG. 5 is a perspective view of a wheel structure incorporating the radiation shield attachment illustrated in FIG. 1.

In the embodiment of the invention illustrated in FIG. 5, the wheel stretcher 14 may incorporate a radiation shield 10' at each end thereof if desired or required. As shown therein, the stretcher 14 generally includes a rectangularly shaped, tubular frame member 58 for mounting a patient support surface 60 and a wheel undercarriage 62 for supporting the frame 58.

The undercarriage 62 as illustrated in FIG. 5, includes a longitudinally extending center support member 64, a base member 66 and four vertically disposed legs 68 one at each corner of the frame 58, and each having a caster wheel 70 mounted at its lower end. Preferably, each leg 68 is a cylindrical, tubular member extending between the base 66 and the frame 58 and its upper end is open for forming a socket for receiving the ends of the radiation shield legs 24' and 24a'. As illustrated, the legs 24' and 24a' may be provided with collars 72 for positioning the attachment 10' on the stretcher 14.

In this embodiment, the laminated shield structure 16' is sized and shaped to extend across the width of the frame structure and vertically extend from below the patient support surface 60 to a height above a supine patient for shielding the attendent wheeling the stretcher 14.

It will be appreciated from the foregoing description that the invention has resulted in a radiation shield which is comprised of a minimum number of components and which can be quickly and easily attached on a wheel patient supporting structure without requiring any particular expertise or tools.

In accordance with the provisions of the patent statutes the principle and mode of the invention have been explained and what is considered to represent its preferred embodiments have been illustrated and described. It should, however, be understood the invention may be practiced otherwise than as specifically illustrated and described without departing from spirit and scope.

What is claimed is:

1. In a wheelchair assembly having a pair of spaced apart side frames and a patient supporting means therebetween, a radiation shield adapted to protect an attendant pushing the wheelchair from radiation applied to a patient sitting in the wheelchair, comprising:
   a flexible sheet of radiation shielding material;
   a pair of spaced apart, generally vertically extending support members attached to said sheet of radiation shielding material; and
   means for attaching each of said vertically extending support members to a respective one of the wheelchair side frames such that said sheet of radiation shielding material functions both as a backrest to support a patient and as a shield to protect an attendant from radiation applied to the patient, said support members and said sheet of radiation shielding material extending upwardly above the head of the patient supported by the wheelchair to provide additional shielding protection for the attendant.

* * * * *